United States Patent
Hickle et al.

(10) Patent No.: US 7,559,483 B2
(45) Date of Patent: Jul. 14, 2009

(54) SMART SUPPLIES, COMPONENTS AND CAPITAL EQUIPMENT

(75) Inventors: Randall S. Hickle, Lubbock, TX (US); Samsun Lampotang, Gainesville, FL (US)

(73) Assignee: Scott Laboratories, Inc., Lubbock, TX (US)

( * ) Notice: Subject to any disclaimer, the term of this patent is extended or adjusted under 35 U.S.C. 154(b) by 0 days.

(21) Appl. No.: 11/898,063

(22) Filed: Sep. 7, 2007

(65) Prior Publication Data

US 2008/0061153 A1    Mar. 13, 2008

Related U.S. Application Data

(62) Division of application No. 10/151,255, filed on May 21, 2002, now Pat. No. 7,299,981.

(60) Provisional application No. 60/291,943, filed on May 21, 2001.

(51) Int. Cl.
    *G06K 19/06*     (2006.01)
(52) U.S. Cl. .................. 235/492; 235/375; 235/383; 235/384; 235/385
(58) Field of Classification Search .......... 235/375, 235/380, 382, 383, 384, 385, 492
    See application file for complete search history.

(56) References Cited

U.S. PATENT DOCUMENTS

| | | | |
|---|---|---|---|
| 4,003,379 A | 1/1977 | Ellinwood, Jr. | 128/260 |
| 4,510,490 A | 4/1985 | Anderson, III et al. | 340/572.1 |
| 4,616,316 A | 10/1986 | Hanpeter et al. | 364/413 |
| 5,305,745 A | 4/1994 | Zacouto | 128/637 |
| 5,313,052 A * | 5/1994 | Watanabe et al. | 235/375 |
| 5,431,627 A | 7/1995 | Pastrone et al. | 604/65 |
| 5,854,591 A | 12/1998 | Atkinson | 340/825.17 |
| 5,882,338 A | 3/1999 | Gray | 604/131 |
| 5,925,066 A | 7/1999 | Kroll et al. | 607/3 |

(Continued)

FOREIGN PATENT DOCUMENTS

CN    87104336 A    2/1988

(Continued)

OTHER PUBLICATIONS

International Search Report, Application No. PCT/US02/15956 dated Oct. 14, 2002.

*Primary Examiner*—Karl D. Frech
(74) *Attorney, Agent, or Firm*—Hogan & Hartson LLP

(57) ABSTRACT

The present invention relates to capital equipment units, such as systems for providing medical treatment, that are associated with smart supplies. The smart supplies are tagged with data carriers which may encode such information as a unique ID for the supply or component, the identification of the supply or component, the identification of the source of the supply or component, the status of whether said supply or component has been previously used, the expiration date of the supply or component, and in the case where the supply or component contains drug, the purity levels of the drug and the concentration levels of the drug. The capital equipment units or their users then utilize the information to assure quality of any procedure run with the units, by way of improved pre-use checks, certification of the supplies for use, record keeping, inventory control, and charge capture.

25 Claims, 4 Drawing Sheets

U.S. PATENT DOCUMENTS

| | | | |
|---|---|---|---|
| 5,980,501 A | 11/1999 | Gray | 604/408 |
| 6,019,745 A | 2/2000 | Gray | 604/131 |
| 6,123,686 A | 9/2000 | Olsen et al. | 604/151 |
| 6,134,470 A | 10/2000 | Hartlaub | 607/14 |
| 6,877,658 B2 | 4/2005 | Raistrick et al. | 235/385 |
| 6,935,560 B2 | 8/2005 | Andreasson et al. | 235/385 |
| 6,976,628 B2 | 12/2005 | Krupa | 235/462.08 |
| 2001/0028308 A1 | 10/2001 | De La Huerga | 340/573.1 |
| 2002/0038392 A1 | 3/2002 | De La Huerga | 710/8 |
| 2003/0004652 A1 | 1/2003 | Brunner et al. | 702/19 |
| 2003/0011476 A1 | 1/2003 | Godfrey | 340/572.8 |
| 2003/0089733 A1 | 5/2003 | Cain et al. | 222/30 |
| 2003/0189058 A1 | 10/2003 | Liff et al. | 221/13 |
| 2004/0008123 A1 | 1/2004 | Carrender et al. | 340/825.49 |
| 2004/0100415 A1 | 5/2004 | Veitch et al. | 343/850 |
| 2004/0138921 A1 | 7/2004 | Broussard et al. | 705/2 |
| 2005/0276728 A1 | 12/2005 | Muller-Cohn et al. | 422/102 |
| 2006/0044206 A1 | 3/2006 | Moskowitz et al. | 343/841 |
| 2006/0097873 A1 | 5/2006 | Vrba et al. | 340/572.1 |

FOREIGN PATENT DOCUMENTS

| | | |
|---|---|---|
| CN | 1493049 A | 2/2001 |
| DE | 197 20 747 C2 | 11/1997 |
| EP | 0250250 | 12/1987 |
| WO | 00/33246 | 6/2000 |
| WO | 01/08106 A2 | 2/2001 |

\* cited by examiner

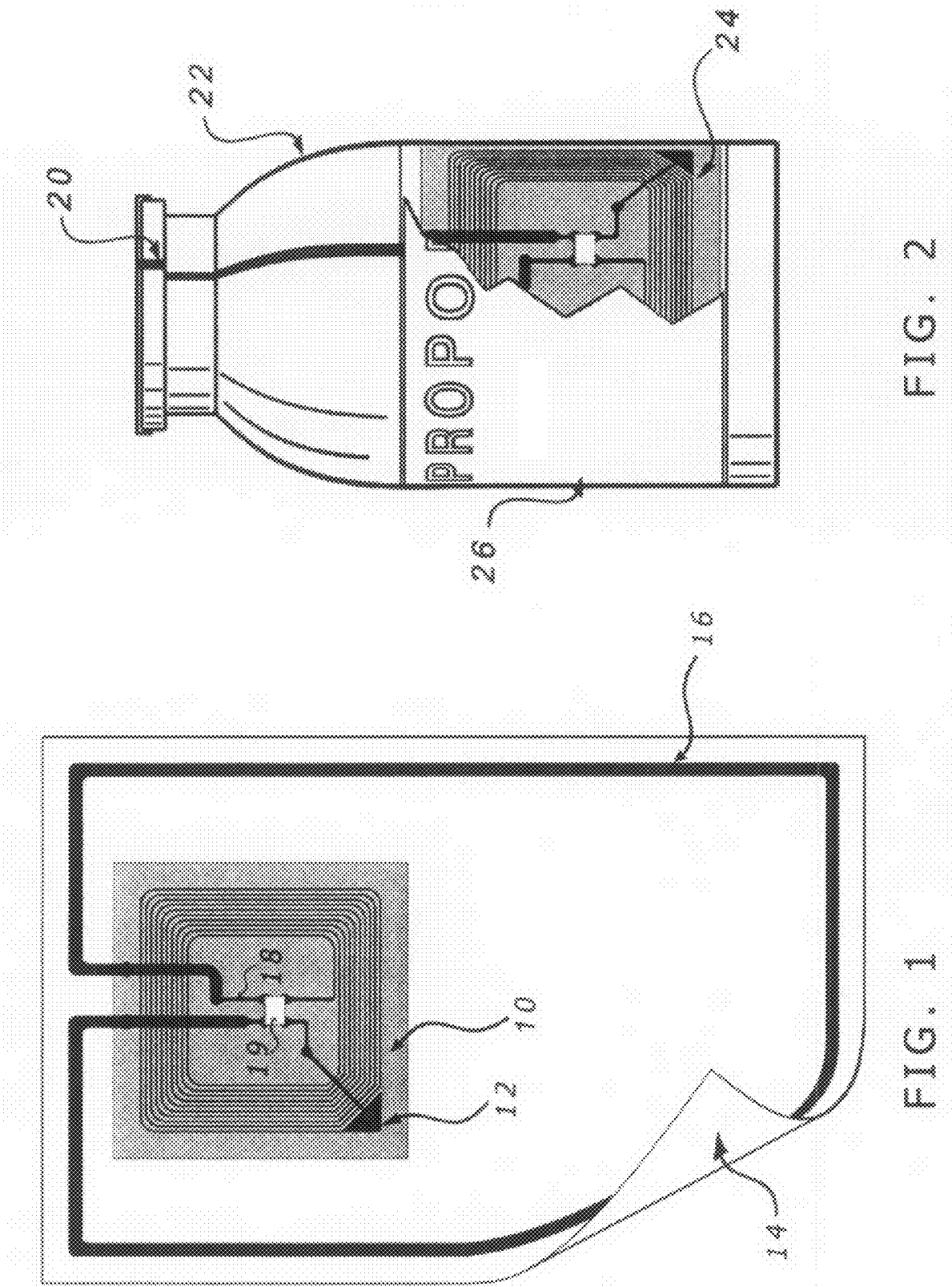

SMART SUPPLIES, COMPONENTS AND CAPITAL EQUIPMENT

CROSS REFERENCE TO RELATED APPLICATIONS

This application is a Divisional of co-pending U.S. patent application Ser. No. 10/151,255, filed May 21, 2002 now U.S. Pat. No. 7,299,981, which claims priority to U.S. Provisional Patent Application No. 60/291,943 filed May 21, 2001 all of which are incorporated herein by reference in their entirety.

FIELD OF THE INVENTION

The present invention relates to product authentication by way of identification and certification of the origin or manufacturer of medical supplies, components, and other devices. Such authentication ensures, among other things, proper fit and operation via quality assurance of appropriate purity, concentration, sterility, calibration and manufacturing tolerance of the devices. The present invention also relates to marking a single patient use medical supply or component as used, once it has been used, in order to prevent cross-contamination with infectious disease between patients.

BACKGROUND OF THE INVENTION

Many medical procedures, such as the administration of drugs (e.g., sedative and analgesic drugs) are safety-critical tasks with patient health at issue. Therefore, identification and certification of the origin and manufacturer of medical supplies and the identification of drugs to be administered to a patient is important. Such identification and certification enhances patient safety by ensuring and enhancing the quality of pharmaceuticals and single-patient use disposable devices, including assuring such criteria as proper purity, concentration, sterility, calibration, and manufacturing tolerance.

Also important are means for preventing medical supplies having already been used with one patient from being subsequently reused with another patient. Cross-contamination between patients is a concern because of infectious diseases caused by blood-borne pathogens such as the Human Immunodeficiency Virus (HIV) and hepatitis B and C, and by respiratory pathogens such as multi-drug resistant tuberculosis. Further, contamination of certain pharmaceuticals have caused fatal cases of septicemia because these compounds support the growth of bacteria.

In an attempt to prevent cross-contamination, medical equipment, components and supplies are often sterilized prior to reuse with a different patient. However, recent studies indicate that sterilization of many medical devices, especially those that have valves, complex mechanisms, or narrow and long lumens (e.g., laparoscopic trocars, endoscopic biopsy forceps, and fiberscopes), may not be entirely effective.

An alternative way to avoid cross-contamination is through single patient use (disposable) medical supplies and components. Disposable medical supplies and components will not prevent cross-contamination if they are reused. Therefore, concerns remain as to both the deliberate and the unintentional reuse of disposable medical supplies and components. There is also concern beyond patient cross-contamination with the unauthorized sterilization and/or reuse of disposable medical supplies and components which are not designed or validated to be sterilized or to have a long service life.

Goods that outwardly and superficially look like a component or supply of a medical device having the appropriate form, fit, and function to be used with the device may actually be uncertified products that were otherwise not manufactured according to original design specifications. In many circumstances where quality and reliability of performance are mission-critical, the customer or other user may not be able to discern the difference between uncertified and genuine parts. For example, proper use of a drug administration or infusion system requires knowledge of the drug concentration, dead space volume in the infusion tubing and drug pump cassette, and calibrated tubing and compression surfaces (in order to generate volumetric control of the rate of drug infusion). This information may not be known or be outside the specifications for uncertified versions of components or supplies of infusion systems.

If medical supplies were "smart," the detection of the presence or absence of certified medical supplies and their use-condition could be easily automated. Automation may also relieve the clinician of the chore and memory load of certifying products and may enhance patient safety by ensuring that all necessary supplies are present and where appropriate, unused, before the initiation of a medical procedure.

Further, despite the best quality assurance efforts of manufacturers, contaminated or defective products sometimes reach the marketplace. Ensuing product recalls are an extremely costly endeavor for the manufacturer. An identification system that would facilitate localization and removal of every single recalled product would be advantageous. As an added safety measure, it would be beneficial if the batch number and unique identification numbers of the recalled products could be programmed into the associated delivery device, like a conscious sedation machine, or at any dispensing location like a pharmacy or a centralized database so that any recalled product, such as a tainted drug vial, slipping through the recall is rejected by the delivery device.

SUMMARY OF THE INVENTION

The present invention provides apparatuses and methods for permitting medical supplies and components to interact with medical capital equipment units (e.g., medical treatment systems such as, among others, sedation and analgesia delivery systems, anesthesia machines and workstations, x-ray machines, dialysis machines) and clinical information systems for the purpose of improving patient safety while enhancing the efficiency of the clinical process flow.

The present invention provides a system for ensuring the safe and efficient use of devices with tamper-evident seals by way of reporting to their users whether the tamper-evident seals are intact and whether inspection or replacement of the devices having the seals is past due. Also, regarding the use of packaged pre-assembled kits that include all the supplies and components required for a particular procedure, medical or otherwise, or individual medical devices, the present invention provides a system which promotes and monitors the unpackaging of such kits and devices just prior to use. Such promotion and monitoring ensures sterility of the kits and individual devices prior to their use with a patient.

Regarding pre-use check sequences for the operation of some medical systems, such as sedation and analgesia administration devices, the present invention provides a system that detects the presence or absence and the use-condition of medical supplies and components required for the operation of the systems. Thus the invention may enhance patient safety by making sure that necessary supplies and components (regular and emergency) are present and functional and where appropriate, unused, before the operation or procedure of the medical systems begins.

One system according to the present invention can track individual drug containers, identify how much drug is used or even wasted, and can thus monitor the efficacy of re-engineered clinical processes designed to reduce waste. In further embodiments of the invention, means for real-time tracking of the identity of a drug in a syringe and its concentration as well as the amount delivered to a patient are provided. Such a tracking function of the invention can flag drugs contra-indicated for the patient when the system is coupled to a computerized medical record that includes the patient's history and physical examination.

The present invention also provides asset tracking and efficient inventory control via a system for tracking and instantly locating mobile capital equipment in a hospital or other setting as well as for monitoring which medical supplies in an inventory and components or supplies are expired or will soon expire. Further a system is provided that facilitates the localization and removal of products recalled by their manufacturers or a regulatory agency.

The present invention also provides a system that can quickly verify whether there are foreign objects left in a surgical cavity without the need for X-ray radiation.

The various information tracking and identification functions described above are made possible by a means of marking medical devices, system components, disposables, consumables, or other products with an indicator or "smart" tag. The invention provides one such indicator tag in the form of a radio frequency identification ("RFID") tag which can be affixed to an article thereby labeling it with certain information that can be read by a nearby reader. An RFID tag may be written to in order to store additional or updated information or it may be employed as a simple use indicator whereby the tag is altered upon its associated article being used in a way that the reader can detect. The invention also provides means for shielding the RFID tags from unintended radio frequencies. Several advantages of RFID tags exist, but the present invention also provides alternative means for marking devices for the above functions. One other such device is an electrical EEPROM tag which can store much information about the article to which it is attached.

BRIEF DESCRIPTION OF THE DRAWINGS

FIG. 1 is a drawing of a radio frequency identification ("RFID") tag combined with a breakable conductive loop;

FIG. 2 is a perspective drawing of an RFID tag with a breakable conductive loop that is used as a label on a vial;

DETAILED DESCRIPTION OF THE INVENTION

Figure 3:
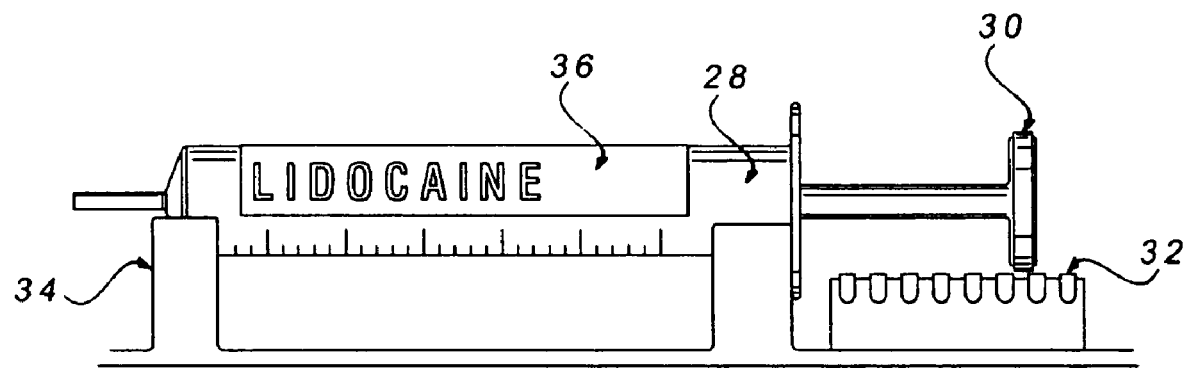
FIG. 3 is a side view of an RFID tag used as a label on a syringe together with at least one linear array of Hall effect sensors.

A recognition sub-system of a medical device system reads and authenticates the identification and/or source of a drug, supply, component or attachment that is associated with a medical device system. Such a medical device system could be a sedation and analgesia delivery system such as that disclosed in U.S. patent application Ser. No. 09/324,759 filed Jun. 3, 1999, the entirety of which is herein incorporated by reference. The sedation and analgesia system of application Ser. No. 09/324,759 includes a patient health monitor device adapted so as to be coupled to a patient and generate a signal reflecting at least one physiological condition of the patient, a drug delivery controller supplying one or more drugs to the patient, a memory device storing a safety data set reflecting safe and undesirable parameters of at least one monitored patient physiological condition, and an electronic controller interconnected between the patient health monitor, the drug delivery controller, and the memory device storing the safety data set; wherein said electronic controller receives said signals and in response manages the application of the drugs in accord with the safety data set. The recognition subsystem of the present invention may be used with such a sedation and analgesia system to further manage the application of the drugs in accord with the identification, source or other information regarding a drug, supply, component or attachment to the sedation and analgesia system. The safety data set, as referred to by the electronic controller, may further include data regarding proper values for the identification and/or sources of such drugs, supplies, components or attachments.

The medical device system associated with the recognition subsystem of the present invention could also be any of numerous other systems that employ drug or other consumable or disposable supplies and components. Examples of other systems with which the recognition subsystem of the present invention could be associated, include, among others, anesthesia systems (e.g., induction machines, anesthesia machines and workstations), imaging systems (e.g., X-ray, MRI, CAT) systems, therapy systems (e.g., radiation and chemo-therapy machines), treatment systems (e.g., dialysis machines), interventional systems (e.g., heart/lung bypass machines, cell savers), and diagnostic systems (e.g., colonoscopes, mammographs).

The present invention provides a means that, if a non-certified or previously used drug, component or supply is attached to an associated medical device system, will prevent a medical device system from initiating the function, or functions, that it is designed to provide. For example, with a sedation and analgesia system, the administration of sedative or analgesic drugs would be prevented in order to ensure the reliability of performance of the system.

Regarding the exemplary medical device system of U.S. patent application Ser. No. 09/324,759, examples of function-critical drug containers, the recognition of which would be performed according to the present invention, include those containing Propofol, remifentanil, dexmedetomidine, or intravenous xenon (xenon dissolved in a lipid emulsion). Similarly, examples of function-critical supplies and components that might be connected to, and used with the noted sedation and analgesia system include a respiratory monitor, oxygen delivery tubing, a drug infusion cassette, drug infusion tubing, a one-way anti-reflux valve, a patient audio earpiece to provide audible prompts for testing or monitoring, and a resuscitation kit.

Function-critical drug containers, supplies, and components are recognized, according to the present invention, by way of a data carrier or "tag" that is associated with them and then read by a reader device. A data carrier is preferably generic in the sense that data is not represented by physical characteristics of a tag (such as its fundamental resonant frequency). The data carrier may also simply indicate the status of an article as used or unused. A data carrier or "tag" may be small (e.g., 3 mm square) and can store relatively large amounts of data. Selected tags preferably have a lifetime that is equal to or greater than the shelf life of products being tagged. Additionally, selected tags may provide data encoding that is generic and not specific to attributes (e.g. physical dimensions or resonant frequency) of a tag. Further, data storage capacity of a tag preferably is sufficient to allow creation of a unique ID number for each individual medical supply or component. An example of a tag that that may be used with the present invention is a radio frequency identification ("RFID") tag. Other suitable electronic tagging technologies include programmable memories like EPROMS, EEPROMS and magnetic strips.

FIG. 1 shows an RFID tag 10 attached to a thin backing 14 that is made of a material, such as a self-adhesive paper, that can be torn by hand. RFID tag 10 consists of a miniature integrated circuit 19 and an antenna 12. A conductive loop 16, that can be implemented with, among other things, conductive ink or fine breakable conducting wire such as copper, is deposited on the backing 14 and is in electrical connection to the integrated circuit 19 via conductive traces and pads 18. The conductive pads 18 also provide physical separation so that the conductive loop 16 can be deposited or connected using conductive glue with coarse resolution on the RFID tag 10. In embodiments where the conductive loop is breakable, when the breakable loop is broken, such as when the thin backing membrane 14 is torn, data in the RFID tag is mechanically reprogrammed.

In a particular embodiment, the invention utilizes a passive, inexpensive, disposable, non-contact, non-volatile read/write radio frequency identification ("RFID") tag to authenticate a medical supply or component and indicate its use status (such as, used, unused, past expiration or inspection date, number of times used) for single-use and multiple-use medical supplies. The reading/writing zones of a reader/writer are advantageously located to encompass the tags of tagged medical supplies when used in conjunction with a capital equipment unit operably coupled to the reader/writer. The RFID reader/writer is attached to or associated with the medical device system and communicates with a CPU of the system. Software resident on the CPU of the system in turn may interface and communicate with other systems like a local area network (LAN), inventory control system, automated charge capture and billing system, medical record system, as well as the Internet and the Web and other Internet- and Web-based applications. Data concerning a smart medical supply or component may also be used by other subsystems of a capital equipment unit, for example, to facilitate and speed a semi-automated pre-use or functional check of the capital equipment unit. A reader/writer could interface to an RFID tag via, among other techniques, inductive coupling (e.g., by using an antenna) or capacitive coupling (e.g., by using conductive carbon ink that picks up electrostatic charges from reader). RFID tags from manufacturers like TI, Motorola, Philips, Mitsubishi, Intermec, Micron and SCS may be used with this invention.

In particular embodiments of the present invention, the amount of data that can be stored in a tag is large enough such that each single tagged item has a unique, individual identification number as well as a batch number. The batch number may form part of the unique identification number or may be separate therefrom. Having enough data storage capability on a tag to assign a unique number to each individual tagged medical supply and component as it makes its way from a manufacturer to a patient enables the creation of powerful databases providing real-time data to improve the efficiency of manufacturing, distribution, warehousing, restocking of medical supplies and components, and reduction of waste.

As an added safety measure in the event of a product recall, the batch numbers and unique identification numbers of recalled products may be programmed into associated medical device systems, such as sedation and analgesia delivery systems or dialysis machines (among others), or at any dispensing locations such as pharmacies, stock rooms and clean rooms. Thus, any tainted drug vial, dialysis cartridge, recalled medical supply or component, or the like, slipping through a recall could be automatically identified and rejected from use upon the system's matching a list of unique identification numbers or batch numbers of recalled products. The list of unique identification numbers and/or batch numbers of the recalled products could be downloaded from the Internet or Web to the medical device system to provide worldwide, quasi-instantaneous and timely dissemination of specific information regarding recalled products, as the information is being updated at a manufacturer's or regulatory agency's web site. The tag may also include among its stored data an address such as a Universal Resource Locator (URL) where updated information about a tagged product such as recall status and newly discovered data such as contra-indications (not to be used with certain drugs, patients, environments or conditions).

The invention also provides a reader/writer on a medical capital equipment unit that selectively reads, or reads and writes to, any given tag among a plurality of tags associated with different disposable and reusable medical supplies and components used in conjunction or associated with the capital equipment unit. The invention also contemplates using more than one reader/writer with a medical capital equipment unit, such as in situations where a single reader/writer embodiment, although cheaper and easier to implement, may not provide enough area coverage or redundancy in applications where at least one of the functions selected from the group of reading and writing is critical. In further embodiments, spare medical supplies and components can be stored in close proximity to, or inside a capital equipment unit, without risk that they are unintentionally written to as "used" when they are actually unused spares.

In particular embodiments of this invention, the recognition subsystem is able to "write" to a medical supply or component that it has been contaminated through use and is no longer suitable for use on subsequent patients. These tagged items may also be packaged along with other supplies in a kit. The kit has integrated into it the ability to be recognized and "read" by the system as quality certified and used or unused and "written to", once used by the system, labeling it as a contaminated article. This reading and writing function may be accomplished in numerous ways as herein described.

For articles susceptible to contamination that are designed for multiple uses, it is possible to provide a "rewrite" function, to enable articles to be re-labeled as suitable for use once they have been properly cleaned and quality certified for re-use. Further, it is possible for the write function to store information regarding the number of cycles of use that an article has experienced and to compare this information to a certified life cycle of uses recommended. This writing function may be accomplished through numerous means described later.

Further features of the read/write system of the present invention may include the read/write device not requiring line of sight, physical contact or close proximity, relative movement or scanning, and allowing simultaneous reading of multiple tags and writing or rewriting to a specific tag in the presence of other tags. More specifically, RFID tags, according to the present invention, are autoclavable and resist dirt, grease, scratches, and wear and tear. More than one RFID tag can be read from or written to at the same time. RFID readers do not require line of sight reading nor direct contact with or relative movement to the tags. RFID readers can read at distances exceeding 4 feet depending on antenna size and power.

In particular embodiments of the present invention, RFID tag 10 is a small (e.g., 1.8"×1.8"), thin (e.g., 0.015" maximum/0.003" minimum), self-adhesive label such as the inductively-coupled Tag-it RFID label from Texas Instruments which features 256 user programmable data bits at 4 feet read range and at 13.56 MHz. Such tags can be substituted for a regular label on a vial (e.g., a vial of Propofol or other drug or any other medical fluid) or other disposable or reusable medical supply or component. As will be appreciated by one skilled in the art, 256 bits can generate $1.2 \times 10^{77}$ (i.e., $2^{256}$) unique ID numbers.

As depicted in FIG. 2, a breakable conductive loop 20 is coated or placed over a drug or medical fluid vial 22 including a pull-tab over the vial stopper. The breakable conductive loop is affixed, for example, using conductive glue, to an RFID tag 24 that is attached to the vial. A conventional label 26 that indicates the contents of the vial is optionally placed over the RFID tag to conceal it. When the pull-tab is removed from vial 22, such as when the user is ready to swab the stopper with alcohol and spike it, the conductive loop is broken. The removal of the pull-tab indicates to an RFID reader/writer that is associated with the medical device with which the vial 22 is used that the vial with the broken conductive loop 20 is the one that is being used and thus is the one that should be written to as used. If spare, unused or unopened vials are also present within the reading/writing range of the RFID reader/writer, they are not written to as used.

A further aspect of the present invention uses a tearable or breakable conductive loop made of conductive ink or material or fine breakable wire made of conductive material like copper to indicate the use status of a product, kit or wrapper. For example, if the loop is intact, a bit in a tag corresponding to the use status will be set to 1. However, once the loop is broken (such as after a package has been opened or a seal broken), the use status bit will be set to 0. The breakable conductive loop could be used, for example, to indicate whether an emergency resuscitation kit has been used since it was last restocked or functionally tested and certified, replacing a mechanical seal currently used for the same function. The breakable conductive loop could also be used for pre-assembled kits. A breakable conductive loop may be placed around a glued edge of a kit package. When the kit is opened, some of the conductive ink or conducting material forming a breakable conductive loop will adhere to the glue and the conductive loop will be broken.

For cost-sensitive applications of the present invention, a read-only tag could be used with the breakable conductive loop. Thus a data bit whose status is determined by the integrity of the conductive loop, representing for example the use status of a product, would be mechanically "programmed", providing a limited "write-once" functionality. Setting a data bit to either 1 or 0 according to the integrity of a conductive loop will be obvious to one skilled in the art. For example, a data bit could store a voltage between 3.5 and 5 V to represent 1 and a voltage between 0 and 1.5 V to represent 0. By connecting a pin connector controlling the state of the data bit to +5V via a conductive loop, the data bit is pulled high (encoding a 1) whereas the same data bit is pulled low (encoding a 0) if the loop is broken.

Alternatively, an RFID label with a conductive breakable loop may be placed on a medical supply or component such that the conductive loop has to be broken before the medical supply or component is used. For example, the label or conductive loop could be placed on top of a stopper or pull-tab in a propofol or other drug or medical fluid vial. Thus, a reader will be able to determine which one of the propofol or other drug vials or medical fluid vials are actually in use and which corresponding concentration to use for dosage calculations and target control infusion. Alternatively, short-range RFID tags can be used for this application.

The status (intact or broken) of the breakable conductive loop can be used to infer the use and/or the sterility status (e.g., unused and sterile or used and unclean) of the medical or non-medical item that is tagged with a read/write or read-only RFID tag. For example, a broken conductive loop generally indicates use or loss of sterility of a formerly airtight package containing sterile products. A broken conductive loop may not always imply use of its associated tagged item. For example, a vial that has not yet been spiked is not yet used even if the pull-tab has been broken. Still, even with this example, the conductive loop being broken still may indicate which vial among a multitude of vials within reading and/or writing range of an RFID reader and/or writer is to be used.

This vial identification concept of the invention can also be implemented with a regular RFID label without a breakable conductive loop, an example being the Tag-It from Texas Instruments. When such regular RFID labels are used, the unused or spare vials within reading/writing range of an RFID antenna may be shielded from the antenna by placing them in a metallic enclosure, such as a metallic drawer, or by placing them in metallized plastic wrappers. Alternatively, RFID antennas with very short range may be used, especially in applications where the RFID antenna's reading and/or writing range does not have to be large, for example, to cover multiple tagged items.

Those skilled in the art will readily appreciate that the utility of the RFID tag embodiments herein disclosed is independent of whether the tag has a breakable conductive loop 44 connected to it. Various ways to protect electronically writable RFID-tagged items from being unintentionally overwritten and identified as used exist, including shielding them in a metallized plastic wrapper. Radio waves cannot penetrate a metallic enclosure and the metallized plastic wrapper may achieve the same functionality. Medical supplies and components may be placed in the metallized plastic wrappers during production to keep them clean or sterile while also shielding them from radio waves.

As seen in FIGS. 1 and 2, self-adhesive RFID labels typically are readily accessible and may therefore be tampered with. For example, an original RFID label on a used medical supply or component might be removed and replaced by an unauthorized RFID label that falsely identifies that a medical supply or component is "unused." To make tampering and/or unsafe reuse harder, the present invention contemplates software of a capital equipment unit that stores the individual ID for each medical supply or component used with it as a means to verify whether the ID of a medical supply or component was copied and used more than once with that particular capital equipment unit. The present invention also contemplates networking machines or capital equipment units to a central databank so that if a copied ID is used on a second machine or capital equipment unit in the network, it can still be identified as being used. As an additional anti-tampering feature, individual identification numbers for each medical supply or component are encrypted and the corresponding decryption algorithm is resident on capital equipment units or a server accessed through the Internet or Web. Tampering is also discouraged by imbedding the RFID tag within a medical supply or component during manufacture, to make it inaccessible or whereby physical access to the imbedded tag would disable the medical supply, e.g., by creating a leak in an otherwise airtight system.

FIG. 3 depicts a label 36 (the label comprising an RFID tag) identifying the contents of a syringe 28 (where the syringe is an example of an item that may be tagged according to the present invention). To identify the identity and concentration of drugs manually administered via syringe, a read-write or read-only RFID tag may be incorporated into self-adhesive, color-coded labels currently used to identify drugs in different syringes. The color-coded labels are affixed to each syringe immediately after drawing each drug, per current clinical practice. The RFID tag has encoded thereon data such as drug identity, concentration, syringe size, a unique ID or batch number, as well as use status of the tagged syringe. Linear movement of a syringe plunger is tracked by placing magnetic ink or material on a perimeter of a proximal end of the plunger. A linear array or arrays of Hall-effect sensors, physically spaced or staggered to provide appropriate resolution of volume measurement picks up residual magnetic fields from the magnetic ink or material, thus tracking linear movement of the syringe plunger and thus volume of the syringe content administered if the cross-sectional area of the syringe barrel is known. The RFID tag may contain, among other data, the identity of a drug, its concentration, and whether the syringe attached to the tag has previously been used on another patient. In such embodiments in which a syringe is tagged, magnetic ink or material may be deposited or placed along the circumference of plunger handle 30 of a syringe 28, i.e., around where the user's thumb is usually placed. At least one linear array of Hall effect sensors 32 may be employed to track the linear movement of the plunger 30 when a drug is manually administered by the user. Guides 34 position and support the syringe such that the plunger handle 30 is in proximity to the array or arrays of Hall effect sensors and in doing so, determine the size of the syringe, so that its cross-sectional area may be determined. More than one linear array of Hall effect sensors may be used if the sensor dimension exceeds a desired spatial tracking resolution. In such a situation, the sensors may be staggered along multiple linear arrays in close proximity to the circumference of the plunger handle 30 so as to provide the desired spatial tracking resolution.

Another embodiment of the present invention includes an RFID tag with a breakable conductive loop attached as an RFID seal to a container that houses a non-medical or medical kit, a supply of components (such as a resuscitation kit for conscious sedation or anesthesia), or a sterile, clean, tested, and certified component of some non-medical or medical equipment. The RFID seal may store the date of inspection, cleaning or certification of the contents inside the container to which the seal is attached. Other data that may be stored in such a seal includes, but is not limited to, the names of the personnel performing a procedure, the cleaning, and the certification and the due dates for the next scheduled procedure, where applicable.

Figure 4:
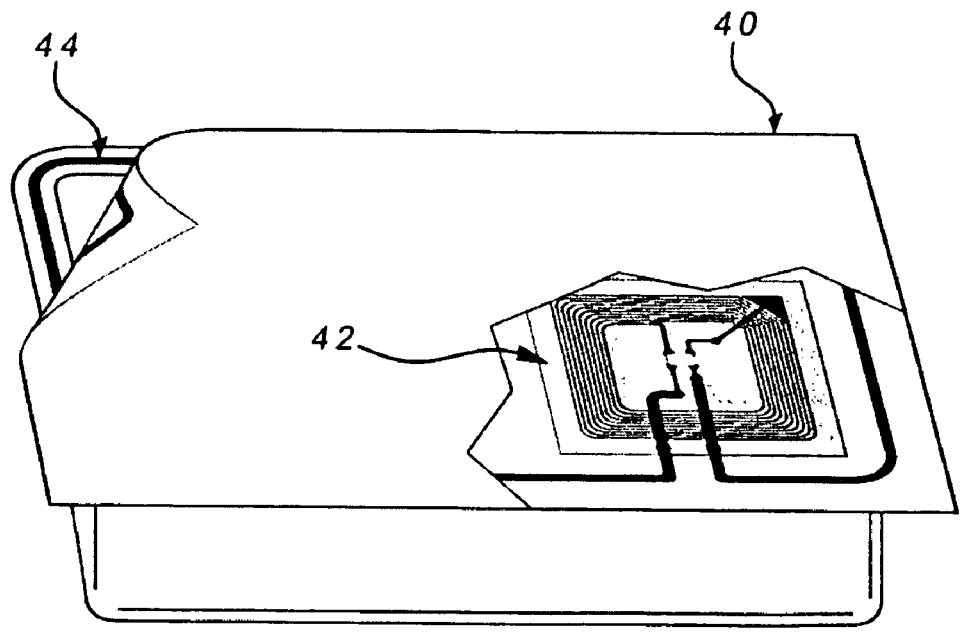
FIG. 4 is a perspective view of a box housing a medical kit or supply or component that is tagged with an RFID label that has a peel away cover.

FIG. 4 depicts a medical kit containing, for example, medical supplies and/or components necessary for a particular procedure or surgery. The kit has a peel-away cover 40. The peel-away cover has an RFID tag 42 attached to it. The RFID tag could be in the form of a label (as shown) or in a non-label format. When cover 40 is peeled away prior to a procedure, breakable conductive loop 44 is broken indicating to a RFID reader and/or writer which kit has been opened and should be written to as being used. This is especially important if, in clinical use, more than one RFID-tagged medical kit, component or supply may be present within the read/write range of the RFID reader/writer of a medical device system. The conductive trace could also be laid out on the internal surface of peel-away cover 40 such that if cover 40 is cut, instead of peeled away, the conductive trace is broken.

The present invention provides for the elimination of the daily checking of back-up equipment for an associated capital equipment unit, (such equipment may include resuscitation kits, all appropriate emergency medical devices, kits of components, the components and supplies, such as, among others, self-inflating resuscitation bags, emesis aspirators, laryngoscopes, endrotracheal tubes, and drugs) are placed in a container that is sealed with a read/write or read-only RFID tag with a breakable conductive loop. The container could be a wheeled cart with drawers or a medical suitcase, among other forms. As long as the RFID seal (a breakable conductive loop) remains intact and the sealed container's contents are not past their due date for inspection (as may be gleaned from the encoded RFID tag), users can have a high level of confidence that all necessary medical supplies and devices required to manage an emergency are present and functioning. The RFID tag on a back-up equipment container may be in the form of a label that includes a tearable or breakable conductive loop that is torn or broken when the container is opened. The RFID label may optionally be self-adhesive. Before use, a container housing a back-up emergency kit is placed within the reading zone of its associated capital equipment unit so that the RFID seal can be read. The RFID tag may contains the due date or due dates for the next inspection or inspections of the back-up equipment as well as the date of the last inspection and names of personnel performing the last inspection or inspections. Thus, a capital equipment unit when used in conjunction with the tagging according to the present invention can automatically inform a user or clinical engineering staff when a kit is past its due date for re-inspection and re-stocking.

In further embodiments that encompass a semi-automated pre-use check of a capital equipment unit and its components, the status of an RFID seal or tag is automatically read. If the seal is broken, indicating the kit may have been used and items may be missing, the user may be warned of such during the semi-automated pre-use check via a user interface system. The pre-use check process may also utilize the tagged information to verify that all required supplies and components are present, unused (if prior use would be a detriment), and not past their expiration dates. The concept of a seal comprising a tag with a breakable conductive element according to the present invention is applicable to any field where it is critical that rarely used equipment be guaranteed as ready and functional when it is eventually needed. Applicable fields, here, could include but are not limited to fire fighting, rescue, emergency response, and the military.

As described above, a passive read/write RFID (or a suitable alternative electronic and/or optical technology) tag may be affixed to a single-patient-use (e.g., a vial of Propofol or other drug or medical fluid vials or gas delivery circuits) or multiple-patient-use (e.g., a monitoring harness) medical supply or component intended to be used with a particular piece of capital equipment (e.g., anesthesia machines or workstations, dialysis machines, sedation and analgesia delivery systems, or X-ray machines) having the ability to read from and write to the RFID tag or other suitable alternative electronic and/or optical technology. A reader/writer on the capital equipment unit is located such that all tags attached to associated supplies and components will be within reading/writing range of the reader/writer device when the tagged medical supplies and components are used in conjunction with the capital equipment unit. Preferably, but not necessarily, the reader/writer is located on the capital equipment unit (such as among others anesthesia machines, sedation and analgesia machines, dialysis machines, X-ray machines) with which a medical supply or component is employed and is interfaced to at least one or more CPU controlling operation of the capital equipment unit. Alternatively, the reader/writer could be tethered (or in wireless communication) to the capital equipment unit but outside it to provide best coverage of tags, or incorporated within a hand-held device such as a personal digital assistant. For purposes of example only, one of the data bits is assigned to represent a used/unused status of a disposable medical supply or component as 0/1 respectively. If the reader reads that the medical supply or component has been previously used (0), then a user can be warned about the danger of cross-contamination and prevented from using a previously used medical item.

A further function of the RFID tags of the present invention is the verification that sponges or surgical instruments have not been inadvertently left in a surgical cavity in a manner that does not incur the undesirable time expenditure or radiation exposure involved with taking a radiograph of the surgical cavity. Surgical instruments and supplies may be tagged with a disposable RFID tag. Scanning a hand-held RFID wand or reader over a surgical cavity will allow detection of any tagged objects left behind. This scanning can be done before the surgical cavity is closed.

Electronic tags may also be used to indicate use and store information about the items to which they are connected. Examples of items that may be tagged with an electronic tag include but are not limited to disposable medical supplies or components, such as an $O_2$ cannula, a propofol vial, an infusion drug pump cassette, a set of infusion tubing, a resuscitation kit, a set of ECG pads, and an earpiece adapted for use by a patient, intended for use with any of the sedation and analgesia delivery system disclosed in U.S. patent application Ser. No. 09/324,759, anesthesia machines, anesthesia workstations, dental machines, veterinary anesthesia machines, dialysis machines, X-ray machines that employ drugs, or other systems that use reusable, consumable or disposable supplies and components. Similarly, electronic tags according to the present invention can be used for authentication and identification of any drug, supply, component or attachment that is attached to a medical device system for use therewith.

Figure 5:
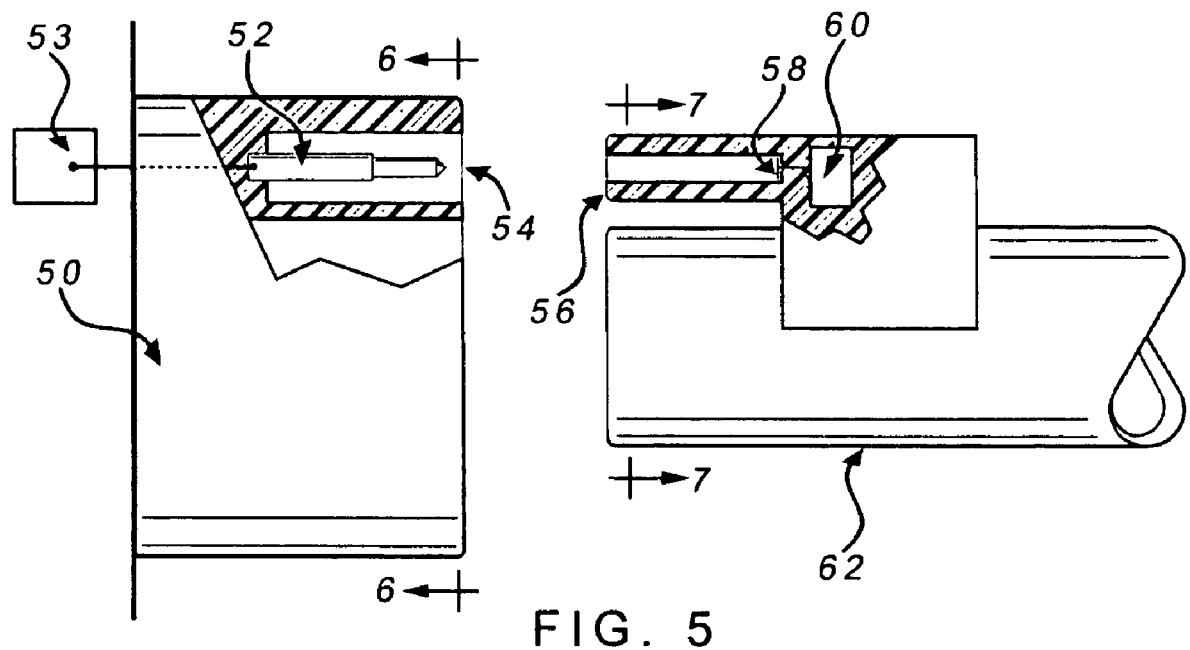
FIG. 5 is a partially-exploded view of an Electrically Erasable Programmable Read Only Memory (EEPROM) tag showing electrical contact between an EEPROM tag embedded in a removable supply or component and an EEPROM reader/writer attached to a capital equipment unit.
Figure 6:
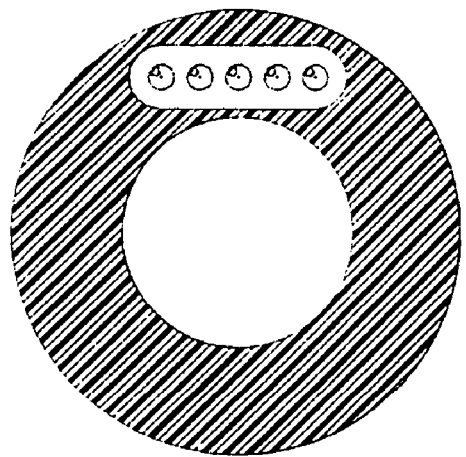
FIG. 6 is a view of a suitable connector on a capital equipment unit for use with EEPROM tagged supplies, components and disposables.
Figure 7:
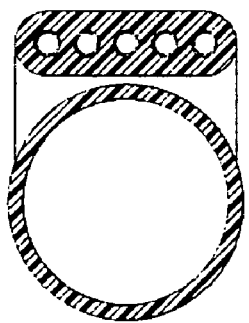
FIG. 7 is a view of a suitable connector on a disposable supply or component for use with EEPROM tagged supplies, components and disposables.

FIG. 5 depicts how an Electrically Erasable Programmable Read Only Memory (EEPROM) integrated circuit ("IC") 60, (e.g., Microchip 24C00) can be embedded into a plastic molding at a machine-interfacing end of a disposable medical supply or other component 62. Circular metallic pads 58 (only one set of which is shown in the figure for clarity) provide electrical connection to pins on the EEPROM. Five circular pads may be used for the following functions: serial clock, serial data, power, ground and detect (used to detect when the EEPROM is plugged in) but more or fewer pads could also be used to implement the electronic tagging concept of the present invention. Circular pads 58 make electrical contact with electrical contacts 52 (e.g., Pogo connectors), which may be spring-loaded and which are housed in connector 50 that is electrically connected to EEPROM reader/writer 53. EEPROM reader/writer 53 may be based on, for example, a Motorola HC12 microcontroller. According to particular embodiments of the present invention, an EEPROM integrated circuit (such as a Microchip 24C00) is embedded into a disposable or re-usable medical supply or component. Data encoded into the EEPROM is read by a microcontroller, such as a Motorola HC12 microcontroller. The microcontroller may also write to the EEPROM. The circular pads are protected inside a cavity formed in male connector 56. Male connector 56 mates to female connector 54 and in doing so provides both indexing and electrical contact between the medical supply or component and the medical capital equipment unit. The purpose of indexing (or keying) is to prevent the medical supply or component from being attached to its associated capital equipment unit or device in an incompatible way or orientation. FIGS. 6 and 7 depict end-on views of the connectors. Those skilled in the art would also appreciate that connectors ensuring electrical contact between an EEPROM and an EEPROM reader/writer can have various other configurations not shown in these figures.

Repeated connection and disconnection of disposable or re-usable supplies and components to the capital equipment may cause the connectors on the capital equipment unit side to wear out thus resulting in poor or intermittent contact. To compensate for this problem, the present invention provides in some embodiments, an electrical connection of the EEPROM tag to the reader/writer unit through a POGO connector, for example, that exerts a mechanical force on the connectors 54 and 56 to ensure good electrical contact. The more costly part of the POGO connector may be placed on the capital equipment side while the less costly part of the POGO connector may be placed on the disposable or re-usable components. Alternatively, the present invention may provide a "middleman" connector between the capital equipment and its associated tagged components. Such a middleman connector may be replaced at periodic intervals or after a particular number of uses, before significant wear occurs.

EEPROM chips may be written to as "used" thus allowing for the prevention of re-use of and thus possible cross-contamination of the supplies or components that are tagged. Alternatively, read only or read/write EEPROMS can also be used to implement tamper-evident seals when combined with a breakable conductive loop.

A write-once EEPROM chip may be used as an electronic tag according to the present invention whereby once one is written to as used it can no longer be identified in any other way. A write-once EEPROM used with a medical supply cannot be rewritten to as being "unused" in situations where it has indeed already been used even if an encryption code and instructions for writing to the EEPROM are available. Thus, write-once chips may provide a means for preventing used supplies from being re-used.

EEPROM tags may also provide other functions for the safe and efficient use of the items they are used to tag. When EEPROM tags that can store sufficient bits, e.g. 128, are used as the tags according to the present invention, each individual medical supply or component having such tags can be assigned a unique ID number and/or encryption code. Such unique identifiers on an EEPROM tag may be used to indicate that a medical supply or component is from a quality, certified, safe, and trusted source, thus providing an authorization function. Authentication may also be made from such information as whether the tagged medical supplies or components have been tested to be compatible with their associated capital equipment unit, whether the tagged medical supplies or components have been recalled or prohibited from use by regulatory agencies, and whether the source of the supplies or components is legal, i.e., licensed to manufacture or supply the supplies or components. EEPROM tags may also facilitate semi-automation of pre-use checks of medical equipment, charge capture and prevention of use of recalled medical supplies and components once the EEPROM tags are in electrical connection with a reader/writer in a capital equipment unit.

Alternatively, magnetic strips like those at the back of credit cards can be used as read/write tags for medical supplies. In such embodiments of the present invention, a read head is implemented to contact the magnetic strip when the strip is moved past the read head. This movement does not need to be constant but cannot be zero. This movement may be obtained when the read head is positioned on a capital equipment unit such that during the physical installation of a tagged medical supply or component with that unit, the tag contacts the read head and moves relative to it. Similarly, upon removal of the medical supply or component from the capital equipment unit after its use, the magnetic strip may also contact a read/write head so that its encoded data is altered or its serial number is logged to indicate that the particular medical supply or component has been used.

Other use-indicating mechanisms may be employed according to the present invention. For example, physical indicators such as thermochromatic ink that changes color on heating or "scratch-and-sniff" coatings may be used in certain situations and on certain items to be tagged. Further, alternative electronic data transfer mechanisms, such as Bluetooth for example, could be used in tagging systems and methods of the present invention.

Figure 8:
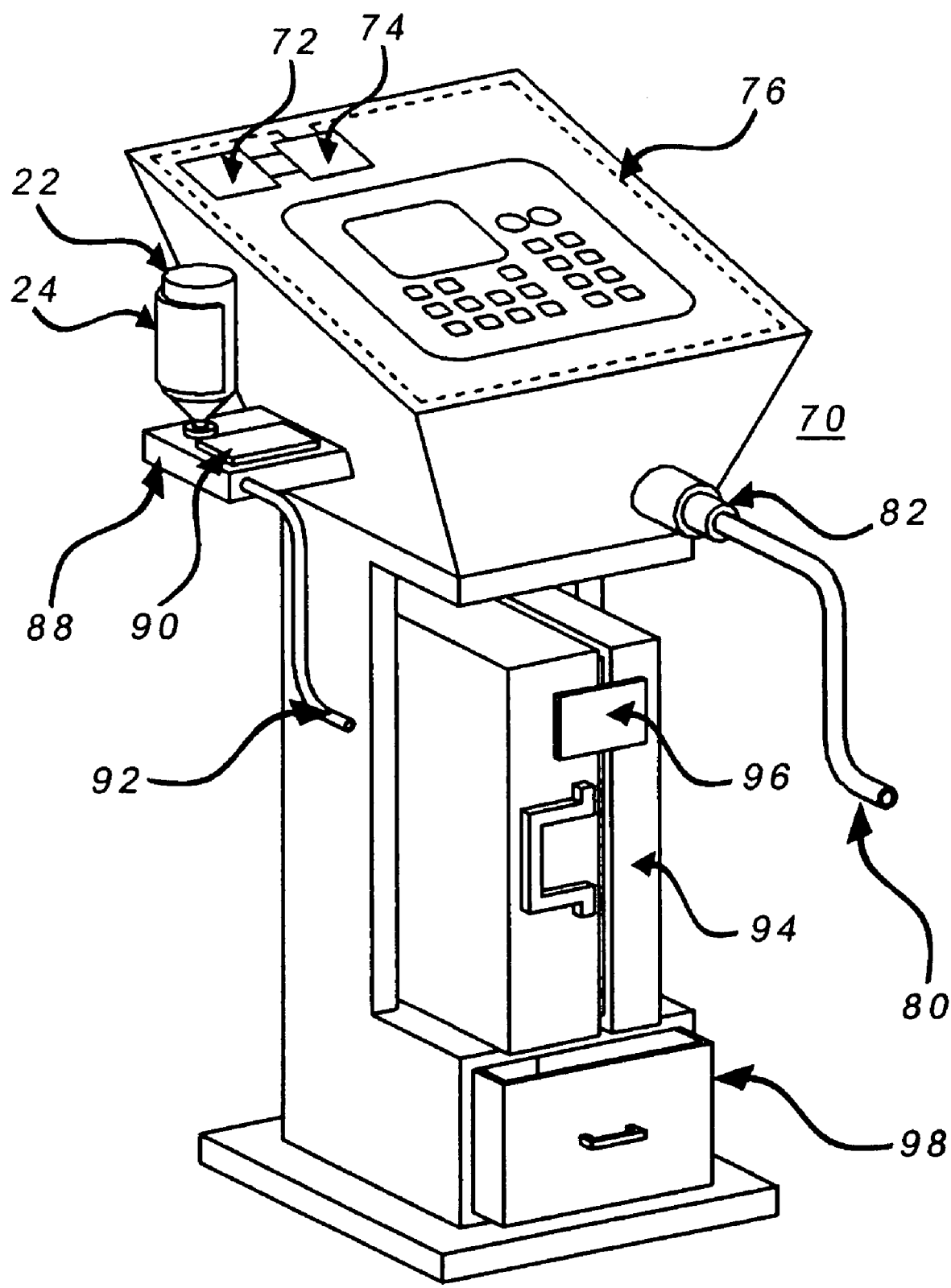
FIG. 8 is a view of a medical device incorporating an RFID reader/writer that interfaces with at least one of an array of RFID tags and seals attached to medical supplies, components, accessories and peripheral equipment.

FIG. 8 depicts an example of a medical device or capital equipment unit 70 that incorporates an RFID reader/writer 72 to interface with various RFID-tagged medical supplies or components according to the present invention. A housed antenna 74 may be connected to an RFID reader/writer 72. Antenna 74 communicates to RFID tags 24, 82, 90 and 96. In embodiments of a medical device or capital equipment unit 70 used with the present invention in which the RFID tags will be located outside the reading/writing range of housed antenna 74, a larger antenna 76 may be implemented by placing a loop of conductive material, such as metal and conductive paint, inside a chassis or frame of the medical device or capital equipment unit. A larger antenna placed in the chassis of medical device 70 has more reading/writing range than the housed antenna. Reader/writer 72 is interfaced to at least one CPU of the capital equipment unit 70, and that CPU can optionally be interfaced with external processing or data sources such as among others a LAN, a WAN, the Internet, and the Web.

If spare medical supplies (e.g., 2 spare propofol vials of different concentrations, in addition to one being used) are present within a reading/writing zone, a reader/writer on a capital equipment unit will detect 3 propofol vials but may not know which concentration to use for propofol delivery calculations or which propofol vial should be written to as "used". In such situations, spare medical supplies stored within the reading/writing range of a reader/writer operably coupled to a capital equipment unit can be placed in a metal enclosure where they are shielded from RF waves.

The concern with RFID-tagged disposable medical supplies and components possibly being unintentionally written to as used may be solved by placing spare medical supplies and components in metallic enclosures, like metallic drawer 98 shown in FIG. 8 to shield the spare RFID-tagged medical supplies and components from the RFID reader/writer.

FIG. 8 also depicts a resuscitation kit 94, as described above, adapted to contain items required for managing an emergency during the use of the medical device or capital equipment unit 70. RFID tag 96 with a breakable conductive loop acts as a seal. The conductive loop is broken when resuscitation kit 94 is opened. A vial 22 for holding medical fluid or a drug such as Propofol is shown tagged with an RFID label 24. The vial is spiked onto a drug cassette 88 that is tagged with an RFID label 90. The disposable or reusable drug cassette snaps onto a peristaltic pump mechanism (not shown) attached to the medical device or capital equipment unit. The peristaltic pump delivers the Propofol or other content of the vial to a patient via intravenous line 92. Disposable or reusable $O_2$ cannula hose 80 is connected to unit 70 and is tagged with an RFID tag 82. All RFID tags and labels are shown placed within reading/writing range of the RFID reader/writer 72.

What is claimed is:

1. An electronic tag for storing and providing information regarding a tagged object, comprising an electronically readable data transmitter coupled to a breakable conductive element, said data transmitter being adapted to transmit previously stored data regarding said tagged object, and said breakable conductive loop causes a first signal to be transmitted with said previously stored data when said breakable conductive material is intact and a second signal to be transmitted with said previously stored data after said breakable conductive material is broken.

2. The electronic tag according to claim 1, wherein said breakable conductive element is formed from conductive material on a breakable seal.

3. The electronic tag according to claim 2, wherein said first signal represents that said tagged object is unused and said second signal represents that said tagged object has been used.

4. The electronic tag according to claim 2, wherein said first signal represents that a package of said tagged object is sealed and said second signal represents that a package of said tagged object has been opened.

5. The electronic tag according to claim 1, wherein said electronically readable data transmitter comprises a radio frequency identification tag.

6. The electronic tag according to claim 1, wherein said electronically readable data transmitter comprises an EEPROM.

7. The electronic tag according to claim 1, wherein said electronically readable data transmitter comprises a readable magnetic strip.

8. The electronic tag according to claim 7, wherein said medical supply or component kit is for use with a sedation and analgesia system.

9. The electronic tag according to claim 8, wherein said electronic data transmitter comprises a read/write memory such that said previously stored data can be altered and said tearable label is adapted to serve as a tamper-evident seal and electronic inventory of an item selected from the group consisting of a medical apparatus, medical equipment storage device, resuscitation kit, medical kit, sedation and analgesia kit, sedation and analgesia resuscitation kit, drug or equipment container, and a drug or equipment package.

10. The electronic tag according to claim 1, wherein said electronic data transmitter comprises a read/write memory such that said previously stored data can be altered by a user of a product attached to said tag or by a reader/writer device.

11. The electronic tag according to claim 1, wherein said electronic data transmitter comprises a read-only memory such that said previously stored data cannot be altered by a user of said tag or by a reader/writer device.

12. An electronically tagged medical supply or component, said supply or component comprising at least one of a mechanical use indicator and a generic electronic data carrier tag, said tag having a first data set that represents information regarding said medical supply or component, and said tag further having a second data set having values dependent upon the physical status of said mechanical use indicator, wherein said first data set and said second data are readable by an electronic data reader or reader/writer.

13. The medical supply or component according to claim 12, wherein said tag is attached to packaging of said medical supply or component and utilizes a data carrier mechanism selected from the group consisting of a radio frequency identification, EEPROM, and magnetic strips.

14. The medical supply or component according to claim 12, wherein said electronic data reader utilizes said first and second data sets to determine according to a predetermined set of rules how a system connected to said reader or reader/writer utilizes said medical supply or component.

15. The medical supply or component according to claim 12, wherein said first data set is read-only.

16. The medical supply or component according to claim 15, wherein said read-only data set represents information regarding at least an identification of said disposable medical supply or component to a medical care system connected to said electronic data reader.

17. The medical supply or component according to claim 12, wherein said tag is a radio frequency identification tag and is inductively coupled to said electronic data reader.

18. The medical supply or component according to claim 12, wherein said tag is a radio frequency identification tag and is capacitively coupled to said electronic data reader.

19. The medical supply or component according to claim 12, wherein said first data set can be electronically written to by said electronic data reader/writer to record a change in a status of said medical supply or component.

20. The medical supply or component according to claim 19, wherein said change in status relates to the status of said medical supply or component as used or unused.

21. The medical supply or component according to claim 19, wherein said change in status relates to the use status of said medical supply or component as the number of uses of the supply or component.

22. The medical supply or component according to claim 19, wherein said change in status relates to the use status of said medical supply or component as the expiration date of the supply or component.

23. The medical supply or component according to claim 12, wherein said mechanical use indicator comprises a breakable conductive loop connected to said tag wherein said loop assigns said second data set a first value when intact and a second value when broken.

24. The medical supply or component according to claim 23, wherein said breakable conductive loop comprises conductive material applied on a breakable seal wherein said breaking of said seal to use said medical supply or component causes said conductive loop to be broken.

25. The medical supply or component according to claim 23, wherein said first data set is read-only.

* * * * *